United States Patent [19]

Schiff

[11] Patent Number: 4,576,142
[45] Date of Patent: Mar. 18, 1986

[54] PERCUTANEOUS INTRA-AORTIC BALLOON AND METHOD FOR USING SAME

[76] Inventor: Peter Schiff, Rte. 7, Cookeville, Tenn. 38501

[21] Appl. No.: 442,958

[22] Filed: Nov. 19, 1982

[51] Int. Cl.$^4$ ............................................. A61M 29/02
[52] U.S. Cl. ..................................................... 128/1 D
[58] Field of Search ................ 128/1 D, 325, 657, 344, 128/772, 0.9; 604/95, 96, 97, 98, 99, 100, 103, 164, 165, 170, 172

[56] References Cited

U.S. PATENT DOCUMENTS

| | | | |
|---|---|---|---|
| 3,426,744 | 2/1969 | Ball | 128/1 D |
| 3,544,668 | 12/1970 | Dereniuk | 604/103 |
| 4,257,427 | 3/1981 | Bucalo | 128/769 |
| 4,327,709 | 5/1982 | Hanson et al. | 128/1 D |
| 4,444,186 | 4/1984 | Wolvek et al. | 128/1 D |

Primary Examiner—W. E. Kamm
Attorney, Agent, or Firm—Louis Weinstein

[57] ABSTRACT

An intra-aortic balloon assembly has a balloon whose distal end terminates in a tip and whose proximal end is joined and communicates with the interior of a catheter tube. A slender stylet extends rearwardly from the tip through the balloon and catheter tube. The balloon is arranged so that its longitudinal axis is significantly displaced from the stylet facilitating tight wrapping of the balloon about the stylet in a single spiral. The stylet may be affixed to the balloon and/or the catheter tube. Coupling means for rotating the stylet are provided for removing any undesired twisting experienced by the stylet during wrapping. The balloon is preferably pre-wrapped and is shipped to the user in the pre-wrapped condition. The balloon is retained in the wrapped condition by a removable holder having releasably joined holder halves encircling the wrapped balloon. Heat shrunk plastic sleeves retain the holder halves in the assembled state. The balloon is pushed out from the holder preparatory to its use, after which the sleeves may be cut away and the holder halves removed. The wrap may further be retained by immersing the balloon in a solution containing a sticky substance which holds the engaging surfaces of the wrapped balloon together. When the wrapped balloon is placed in the bloodstream, the sticky substance dissolves enabling the balloon to easily unwrap.

34 Claims, 16 Drawing Figures

PERCUTANEOUS INTRA-AORTIC BALLOON AND METHOD FOR USING SAME

FIELD OF THE INVENTION

The present invention relates to intra-aortic balloon assemblies and more particularly to method and apparatus for tightly wrapping the balloons of said assemblies and for holding the wrapped balloon preparatory to insertion and particularly insertion employing a percutaneous technique.

BACKGROUND OF THE INVENTION

The use of intra-aortic balloon assemblies for assisting the pumping action of the heart are well-known. Recently, research efforts have placed emphasis upon facilitating the insertion and placement of such balloon assemblies. One of the major objectives is to obtain reductions in balloon profile, i.e. outer diameter, in order to achieve the aforementioned results. Early efforts to achieve such results led to the technique of evacuating the balloon and wrapping the evacuated balloon about an elongated member substantially coaxial with the longitudinal axis of the balloon. This technique is disclosed in U.S. Pat. No. 3,939,820 issued on Feb. 24, 1976 to Grayzel et al. Another technique adopted to achieve substantially similar results utilizes a twistable, elongated stylet coaxial with the longitudinal axis of the balloon, one end of the balloon being rotatable relative to the opposing end, and being twisted about the stylus in order to reduce the balloon profile. This technique is disclosed in U.S. Pat. No. 4,261,339 issued Apr. 14, 1981 in the name of Hanson et al. A novel improvement on this technique is disclosed in application Ser. No. 253,680, filed Apr. 13, 1981, now U.S. Pat. No. 4,422,447, issued Dec. 27, 1983, in the name of the inventor of the present invention, and disclosing an intra-aortic balloon assembly having a stylet rotatable through a manually operable control knob arranged remote from the balloon, for wrapping the balloon.

The balloons of the above techniques which employ a flexible stylet may be introduced into the body through a percutaneous technique such as, for example, the Seldinger technique, wherein an introducer sheath is initially introduced into the body and the balloon is thereafter introduced into the body by insertion into and through said introducer sheath, which may then be either partially or totally removed after the balloon has been properly placed.

Still another technique for reducing the profile of the balloon but without either wrapping or twisting, is disclosed in U.S. Pat. No. 4,327,709 issued on May 4, 1982, to Hanson et al, and describing a technique in which the balloon is evacuated to form a flat tape-like cross-section with the stylet lying along the central axis thereof. The two halves of the balloon lying on either side of the stylus are folded over to form first and second longitudinal folds. The balloon is thereafter inserted into one end of an insertion sheath used in the performance of the Seldinger technique. This technique assumes that the balloon will form a sufficient number of additional longitudinal folds to enable its insertion into the insertion sheath.

Although all of the above-mentioned techniques tend to reduce the profile of the balloon, they nevertheless exhibit certain disadvantages. For example, the balloon assemblies which rely upon twisting techniques create a large number of folds to generate a non-uniform helical pattern which may damage the introducer sheath and/or the patient or the balloon itself, which is greatly stressed by such wrapping. The balloon assemblies adapted for folding and/or wrapping techniques also create a large number of folds, due to their geometry and thus all of the above techniques fall short of reaching a minimal outer profile and without introducing additional disadvantages. In addition thereto, none of the above techniques teach a pre-wrapped balloon, or a method or means for maintaining a pre-wrapped balloon in the fully and tightly wrapped state, until it is ready for insertion.

BRIEF DESCRIPTION OF THE INVENTION

The present invention is characterized by comprising an intra-aortic balloon assembly and method and apparatus for tightly wrapping the balloon of the aforesaid assembly to achieve a small profile not heretofore obtainable through conventional techniques and further including method and apparatus for retaining the balloon in the fully and tightly wrapped state until it is ready for insertion.

The intra-aortic balloon assembly of the present invention comprises a balloon having its distal end terminating in a tip and having its proximal end joined and communicating with the distal end of an elongated catheter tube. A flexible slender stylet extends rearwardly from said tip through said balloon and into said catheter tube. The ends of the balloon joining said tip and said catheter tube are each displaced from the longitudinal axis of said balloon. Said openings position the stylet along an imaginary line which is displaced a substantial distance from the longitudinal axis of the balloon so that the stylet preferably rests against the interior surface of the balloon along the entire length thereof. The juxtaposition of the balloon axis relative to the stylet enables the balloon to be wrapped more tightly and more easily than any of the conventional designs.

Wrapping is accomplished by evacuating the balloon so that it forms a flat, tape-like cross-section. However, contrary to conventional designs, the stylet rests against the interior surface of one of the folds of the flattened balloon enabling the balloon to be wrapped about the stylet in a single, continuous, tight spiral. In order to further assure the positioning of the stylet within a longitudinal fold of the balloon, the stylet may be embedded within the wall of the catheter tube, either through the employment of an extrusion technique or by forming the catheter tube of first and second concentric sleeves and placing the stylet between said sleeves. The stylet may also be joined to the interior surface of the balloon. The stylet is also preferably offset within the distal tip.

The stylet is preferably a slender, flexible stainless steel member. However, the stylet may be a hollow tubular member adapted to receive and pass along a guide wire arranged within the insertion sheath and employed for guiding the intra-aortic balloon into position in one version of the Seldinger technique. The hollow stylet may also be used for monitoring patient blood pressure at the balloon tip from the balloon luer connector.

The offset arrangement of the balloon axis relative to the distal tip and catheter tube, and hence relative to the stylet, permits the user to orient the balloon within the aortic arch to achieve optimum pumping efficiency. Proper orientation is achieved by placement of visible indicia along the exterior periphery of the catheter tube at a location sufficiently remote from the balloon to assure that the locating indicia is outside of the body of the patient when the balloon is in its proper position, and thereby facilitate rotation of the catheter tube and hence the balloon to facilitate proper and, in fact, optimum orientation of the balloon within the aortic arch.

In wrapping the balloon after evacuation thereof, the stylet may experience some undesired twisting. The manually operable control knob permits twisting or rotation of the stylet in the reverse direction to compensate for the undesired twisting which may result from the wrapping operation.

Since the exterior surface portion of the balloon (when evacuated to a tape-like configuration) extends along a path which is greater in length than the interior surface portion of the balloon as it is being wrapped in spiral fashion, these two surface portions tend to move relative to one another. In order to facilitate this movement, and thereby insure a tight wrap, the interior surface of the balloon may be coated with a lubricant. The lubricant may be either a dry or wet lubricant. One liquid lubricant which may be utilized is water which may be removed and evaporated after the wrapping operation. The dry lubricant may comprise a Teflon 1 (i.e. tetrafluoroethylene) powder. Any comparable lubricant may be employed.

In order to maintain the balloon tightly wrapped and in readiness for insertion, the invention contemplates the employment of holder halves which, when releasably joined to one another, encircle the wrapped balloon and retain the balloon in the tightly wrapped condition. At least the interior semi-annular periphery of the holder halves engaging the wrapped balloon is formed of, or coated with, a low friction surface which permits the balloon to be easily pushed out of the holder assembly and into the insertion sheath. The holder halves are held joined to one another preferably through the use of two or more sections of heat shrinkable plastic sleeves which tightly encircle the joined holder halves.

The holder assembly may be removed from the balloon assembly by severing the plastic sleeves. The interfitting of the holder halves by tongue in groove joints permit the sleeves to be severed by a sharp instrument without any danger of accidentally cutting any portion of the intra-aortic balloon assembly contained within the holder assembly.

The balloon may be maintained in the tightly wrapped fashion through the use of a sticky substance applied to the exterior surface of the balloon preparatory to wrapping and retaining the balloon in the tightly wrapped condition by causing engaging surfaces of the balloon to adhere to one another. The sticky substance, which may, for example, be sugar, dissolves immediately upon entry into the bloodstream and is totally compatible with and nontoxic to the body fluids, thereby facilitating unwrapping of the balloon once in place, and without in any way causing any physical damage or chemical unbalance.

It is, therefore, one object of the present invention to provide an intra-aortic balloon design which facilitates wrapping of the balloon portion in a tight, continuous spiral about a stylet. The "old art" of wrapping also acts to "eliminate" the outer, longer, peripheral circumference since the outer circumference of the wrapped balloon "uses up" this length. The larger longitudinal periphery is "no factor" in the new folding technique of this invention.

Still another object of the present invention is to provide an intra-aortic balloon assembly which utilizes a lubricant to facilitate tight wrapping of the balloon portion thereof.

Still another object of the present invention is to provide an intra-aortic balloon assembly in which a stylet extends through the entire length of the balloon portion thereof and wherein the shape of the balloon portion positions the stylet along an imaginary line which is substantially offset from the longitudinal axis of the intermediate portion of the balloon to facilitate tight wrapping thereof.

Still another object of the present invention is to provide a holder assembly for intra-aortic balloons which retains the balloon in a tight wrap preparatory to use and permits easy removal from the holder assembly merely by pushing the intra-aortic balloon assembly through the holder assembly.

Still another object of the present invention is to provide a novel method and apparatus for tightly wrapping intra-aortic balloons and the like in which the interior surface of the balloon is lubricated to facilitate tight wrapping thereof.

Still another object of the present invention is to provide a novel method and apparatus for tightly wrapping the balloon portion of an intra-aortic balloon assembly by coating the exterior surface of the balloon portion with a substance which becomes sticky as it dries, causing the engaging exterior surfaces of the balloon portion to adhere to one another when dried, to maintain the tight wrap, said dried sticky substance being totally dissolved in the bloodstream to facilitate unwrapping of the balloon.

Still another object of the present invention is to provide an intra-aortic balloon assembly in which the longitudinal axis of the balloon portion is offset from the longitudinal axis of the catheter tube joined to the balloon portion, wherein location indicia is provided along said catheter tube to facilitate optimal orientation of the balloon within the body of the patient.

The above, as well as other objects of the present invention, will become apparent when reading the accompanying description in conjunction with the drawing, in which.

DETAILED DESCRIPTION OF THE INVENTION AND THE PREFERRED EMBODIMENTS THEREOF

Figure 1:
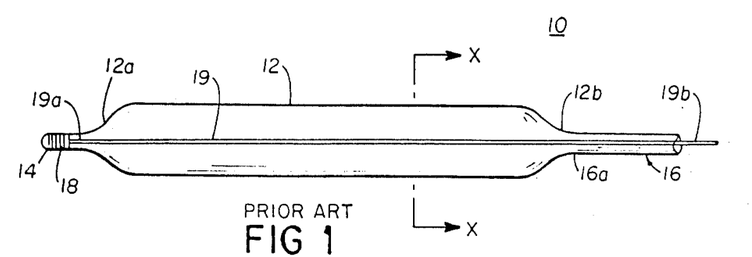
FIG. 1 shows a plan view of a prior art intra-aortic balloon.
Figure 1A:
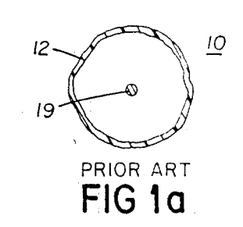
FIG. 1a shows a cross-sectional view of the balloon assembly of FIG. 1 looking in the direction of arrows X—X and with the balloon in the quiescent state.
Figure 1B:
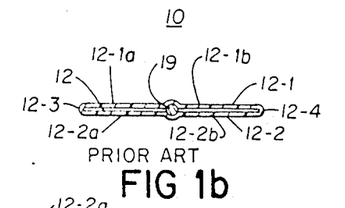
FIG. 1b is a sectional view looking in the direction of arrows X—X of FIG. 1 and with the balloon in the evacuated state.
Figure 1C:
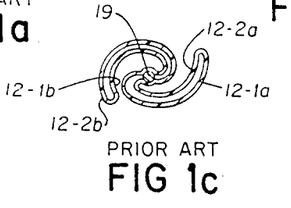
FIG. 1c is a cross-sectional view looking in the direction of arrows X—X of FIG. 1 and showing the manner in which the balloon may be wrapped.

FIGS. 1 through 1c show a prior art intra-aortic balloon assembly 10 comprised of a balloon portion 12 formed of a suitable plastic material which is flexible and bendable to permit the balloon to collapse when evacuated and to permit the balloon to form an annular cross-section when inflated. However, the balloon material is substantially non-stretchable, so as to prevent balloon 12 from stretching during operation within a normal pressure range.

The distal end 12a of balloon 12 is tapered and terminates in a tip 14 which is preferably rounded to facilitate its insertion into the body and to prevent the balloon tip from damaging anything which it engages. The tip may be provided with a radiopaque member 18 which shows up well in fluoroscopes and/or X-rays and is useful in assuring proper placement of the balloon within the human body.

The balloon proximal end 12b is tapered in a similar fashion and merges with the distal end 16a of a hollow, flexible, elongated catheter tube, arranged to couple the balloon to a source (not shown) of selectively positive and negative pulsatile pressure respectively inflating and deflating the balloon in synchronism with the pumping of the heart. Although not shown for purposes of simplicity, it should be understood that catheter tube 16 is of a length sufficient to have its proximal end extend outside of the body when the balloon 12 is properly positioned.

The balloon assembly 10 further includes a slender, flexible, elongated stylet 19, whose distal end terminates in tip 14. Stylet 19 extends rearwardly from tip 14 through the entire length of balloon 12 and into catheter 16. The stylet serves as the means about which the balloon 12 is wrapped or twisted, depending upon which of these two techniques is employed.

FIG. 1a shows a cross-section of balloon 12, wherein it can be seen that stylet 19 is coaxial with the longitudinal axis of balloon 12 when in the quiescent state. In the latter state, the balloon assumes an annular cross-section which is not perfectly circular, but is nearly so, as shown in FIG. 1a.

When it is desired to insert the balloon assembly 10 in accordance with one of the above-mentioned prior art techniques, a vacuum V may or may not be drawn through catheter 16, evacuating balloon 12, causing the balloon 12 to assume the tape-like cross-section shown in FIG. 1b and which is defined by two substantially flat surface portions 12-1 and 12-2, integrally joined to one another along folds 12-3 and 12-4. As can be seen from FIG. 1, stylet 19 is coaxial with the longitudinal axis of balloon 12.

In accordance with one technique, the balloon in the configuration shown in FIG. 1b is folded to form folds respectively intermediate the left-hand fold 12-3 and stylet 19, and intermediate to right-hand fold 12-4 and stylet 19. The balloon, in this folded state, is then inserted into an insertion sheath which causes the balloon to form additional folds in order to facilitate its passage along the insertion sheath.

The balloon 12 may also be wrapped after evacuation. The balloon is first evacuated to form the tape-like cross-section shown in FIG. 1b, the flat portions of the balloon extending to opposite sides of stylet 19 in a manner shown in FIG. 1c. Thereafter the two halves of the balloon 12 are spirally wrapped about centrally located stylet 19, as shown in FIG. 1c. The disadvantage of this arrangement resides in the fact that two separate spirally wrapped halves of the balloon 12 are formed about stylet 19. Since the outer balloon portions, i.e. right-hand half 12-2b of balloon portion 12-2, and the left-hand half 12-1a of balloon portion 12-1 (note also FIG. 1b) form the outside of these spirals, these balloon portions extend over a longer path than the "inside" balloon portions 12-1b and 12-2a, thereby contributing to a nonuniform spiral wrapping of balloon 12. Since the spiral is made up of four surface layers, the nonuniformity is greatly multiplied, making it difficult to obtain a tight wrap, and further contributing to a nonuniform spiral wrapping.

Figure 2:
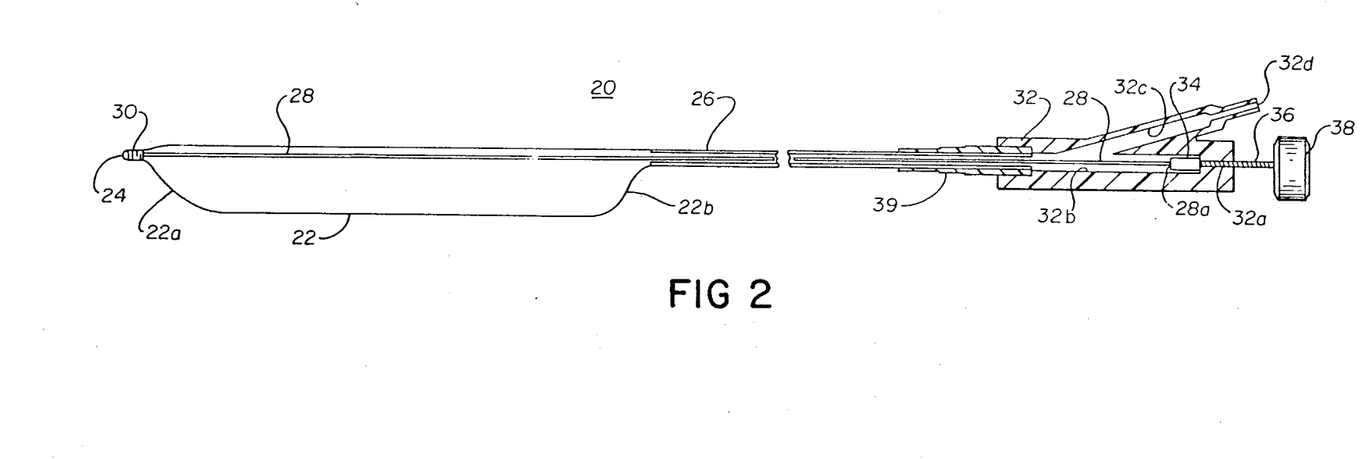
FIG. 2 is a plan view showing an intra-aortic balloon assembly embodying the principles of the present invention.

FIG. 2 shows an intra-aortic balloon assembly 20 designed in accordance with the principles of the present invention and comprised of a balloon 22 tapering at 22a and air-tightly joined to tip 24 at its distal end. Its proximal end 22b is tapered as shown, and is joined to catheter tube 26. A stylet 28 has its distal end extending into tip 24. Stylet 28 extends rearwardly through balloon 22 into catheter tube 26 and coupling member 32 and has its proximal end 28a joined to a solid cylindrical member 34 joined to the free end of an elongated threaded member 36 whose opposite end is secured to control knob 38. Threaded member 36 threadedly engages a tapped opening 32a in coupling 32.

Stylet 28 extends through a central opening 32b in coupling 32 and has its proximal end 28a coupled to member 34. A central bore 32b extends rearwardly and communicates with opening 32c for coupling with means (not shown) for selectively providing positive and negative pulsatile pressure for respectively inflating and deflating balloon 22, preferably in a predetermined relationship with the pumping of the patient's heart.

The distal end of stylet 28 is preferably secured within tip 24 so that any rotation of stylet 28 is imparted to tip 24. Tip 24 may also be provided with a radiopaque member 30, visible on a fluoroscope or in an X-ray for facilitating proper positioning of the intra-aortic balloon assembly 20.

Although not shown for purposes of simplicity, it should be noted that catheter tube 26 has a length sufficient to assure that coupling 32 is exterior to the body of the patient when balloon 22 is properly positioned.

Figure 2A:
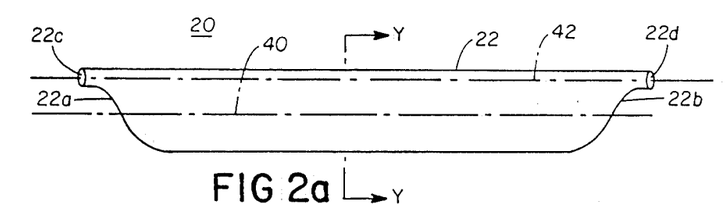
FIG. 2a shows a perspective view of the balloon portion of FIG. 2.

FIG. 2a shows in enlarged perspective view of balloon 22. The intermediate portion of balloon 22 defines a substantially annular cross-section when in the quiescent state, as shown in FIG. 2a. The intermediate portion is substantially concentric about a longitudinal axis represented by phantom line 40. The tapered portions 22a and 22b are generally in the form of non-concentric cones of revolution which cause the openings 22c and 22d to be offset from longitudinal axis 40 and to have their centers lie along phantom line 42, which passes through the centers of openings 22c and 22d and can clearly be seen to be substantially offset (i.e. displaced) from phantom line 40. As can clearly be seen from FIG. 2, stylet 28 passes through openings 22c and 22d and thereby is coaxial with imaginary line 42 and is similarly significantly displaced from imaginary line 40.

Figure 2B:
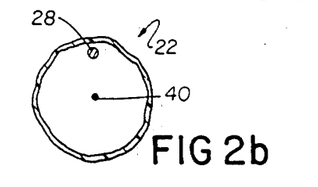
FIG. 2b is a sectional view of the balloon portion of FIG. 2a looking in the direction of arrows Y—Y and showing the balloon portion in the quiescent state.

FIG. 2b shows a cross-sectional view of the intermediate portion of balloon 22 where it can be seen that stylet 28 lies in close proximity to the interior surface of balloon 22.

Figure 2C:
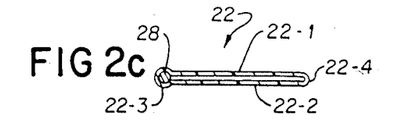
FIG. 2c is a sectional view looking in the direction of arrows Y—Y of FIG. 2a and showing the balloon in the evacuated state.

FIG. 2c shows the balloon 22 after having been evacuated by drawing a vacuum through coupling 32. It can be seen that the balloon forms a tape-like cross-section similar to that formed by balloon 12 as shown in FIG. 1b, in which surface portions 22-1 and 22-2 are substantially flat and are integrally joined to one another along folds 22-3 and 22-4. Stylet 28 is positioned within the interior of fold 22-3, as shown.

Balloon assembly 20, shown in FIGS. 2–2c, may be wrapped in a tight spiral in the following manner:

The balloon is evacuated by drawing a vacuum through coupling 32 to form the cross-sectional configuration shown in FIG. 2c. While maintaining the vacuum condition, the balloon 22 is wrapped in a single spiral about stylet 28. Since the inside portion 22-1 in FIG. 2d must be slightly shorter than the outside portion 22-2, it may be necessary to periodically relieve and re-apply the vacuum to allow sections 22-1 and 22-2 to slide freely with respect to one another during wrapping. The arrangement of stylet 28 within the interior of one fold of the flat balloon forms only a single tape-like portion which is wrapped about stylet 28 in the manner shown in FIG. 2d. Thus, the balloon 22 is wrapped in only a single spiral about stylet 28 as shown in FIG. 2c reducing the total number of layers wrapped about stylet 28 from 4 to 2, and further reducing the inside and outside differential distances wrapped about the stylet 28 from 4 to 2, thus lending itself to the formation of a much more uniformly wrapped balloon which wrap forms a tighter spiral than is capable of being obtained from the balloon configuration shown in FIGS. 1 through 1c. In addition, only one tape-like portion need be manipulated during the wrapping operation of the balloon 22, whereas two separate tape-like portions must be manipulated when wrapping balloon 12, as shown best in FIG. 1c.

During the wrapping operation, the tight wrapping of balloon 22 about stylet 28 may impart some undesirable twisting to stylet 28. In order to relieve this condition, control knob 38 may be rotated through a portion of a revolution in a direction to ease the twisting of stylet 28 at various intervals throughout the wrapping operation. For example, balloon 22 may be wrapped through one or two revolutions about stylet 28, the wrapping operation interrupted momentarily while holding the balloon 22 in the partially wrapped state, and slightly turning knob 38 in the direction to ease any rotation experienced by stylet 28 which may, for example, impart an undesired torsional force upon the end of stylet 28 extending into catheter tube 26 relative to the end of stylet 28 connected to tip 24.

The stylet 28 may be free of the interior surface of balloon 22, or alternatively may be secured to the interior surface by suitable means such as by cementing or bonding the same thereto. This may be accomplished, for example, by coating stylet 28 with a thin layer of a plastic such as polyurethane which is often used to fabricate balloon membrane 22. This layer of polyurethane on stylet 28 can then readily be solvent-bonded to the balloon membrane 22.

Figures 2D, 2E, 2F, 2G:
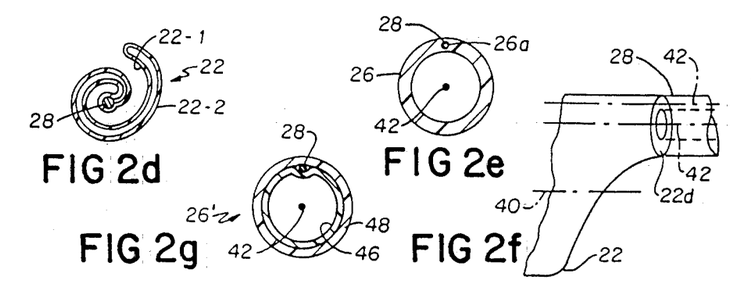
FIG. 2d is a sectional view looking in the direction of arrows Y—Y of FIG. 2a and showing the manner in which the evacuated balloon is wrapped.
FIG. 2e shows a sectional view looking in the direction of arrows Z—Z of FIG. 2.
FIG. 2f shows a sectional perspective view showing an alternative embodiment thereof.
FIG. 2g shows a sectional view of another alternative embodiment for the arrangement of FIGS. 2e and 2f.

In order to be further assured that stylet 28 is positioned in close proximity to, and preferably engaging the interior surface of, balloon 22, catheter tube 26 may be formed in an extruded manner and provided with an opening 26a in the tube wall of catheter tube 26 for receiving stylet 28 as shown in FIGS. 2e and 2f. This arrangement thus offsets stylet 28 from the central axis 42 of catheter tube 28, and hence opening 22d in balloon 22. Thus catheter 28 is not only displaced from longitudinal axis 40 shown in FIGS. 2 and 2f, but is also displaced from imaginary line 42 and is thereby positioned even closer to the interior surface of balloon 22. As an alternative arrangement to that shown in FIG. 2e, catheter tube 26 may be formed in the alternative manner as shown by catheter 26', in FIG. 2g, and comprising concentrically arranged inner and outer sleeves 46 and 48 respectively with stylet 28 being arranged between the exterior surface of inner sleeve 46 and the interior surface of outer sleeve 48, thus displacing stylet 28 from central axis 42 and placing stylet 28 in closer proximity to the interior surface of balloon 22 similar to that shown in FIG. 2f so as to lie well within interior fold 22-3 as shown in FIG. 2b.

Due to the difference in the lengths of the inside and outside portions 22-1 and 22-2 of balloon 22, it is desirable to promote sliding movement therebetween to accomplish the wind-up. In order to accomplish this, a lubricant is introduced into the interior of balloon 22. One suitable lubricant is water in an amount at least sufficient to wet the interior surface of balloon 22. The water is introduced prior to evacuation of the balloon and the balloon is wrapped immediately after its evacuation. The water remaining within the balloon after the wrapping operation substantially evaporates prior to use. However, the amount of water within the balloon 22 is so small as to have a negligible effect upon its efficacy.

The lubricant employed may also be any other liquid or paste-like lubricant having the characteristics of providing lubricating action and being fully compatible with the components of the pumping system with which it interfaces, as well as being nontoxic to the body of the patient in which the balloon is inserted. Other suitable lubricants may, for example, be Freon (fluorocarbon).

As a further alternative, a dry lubricant, and preferably a dry lubricant in powder form, may be employed. The dry lubricant may, for example, be a Teflon powder lubricating the interior surface of the balloon 22, to facilitate wrapping. Alternatively, any dry lubricant having similar properties may be provided.

Once the balloon 12 is wrapped, suitable means must be provided for maintaining the balloon 22 in the tightly wrapped condition. Although retaining the balloon in the evacuated state retains the balloon in the flat, tape-like configuration, the vacuum condition will not hold the balloon in a tight spiral. A novel and unique arrangement for retaining the balloon in the tightly wrapped condition is embodied in the holder assembly 50 shown in FIGS. 3 and 3a which is comprised of a pair of elongated holder halves 52 and 54 having a substantially semi-circular cross-sectional configuration. The circular outer peripheries 52a and 54a are slightly greater than a half circle, as can best be seen in FIG. 3a, and are provided with shallow recesses 52a-1 through 52a-3, and 54a-1 through 54a-3.

Figure 3:
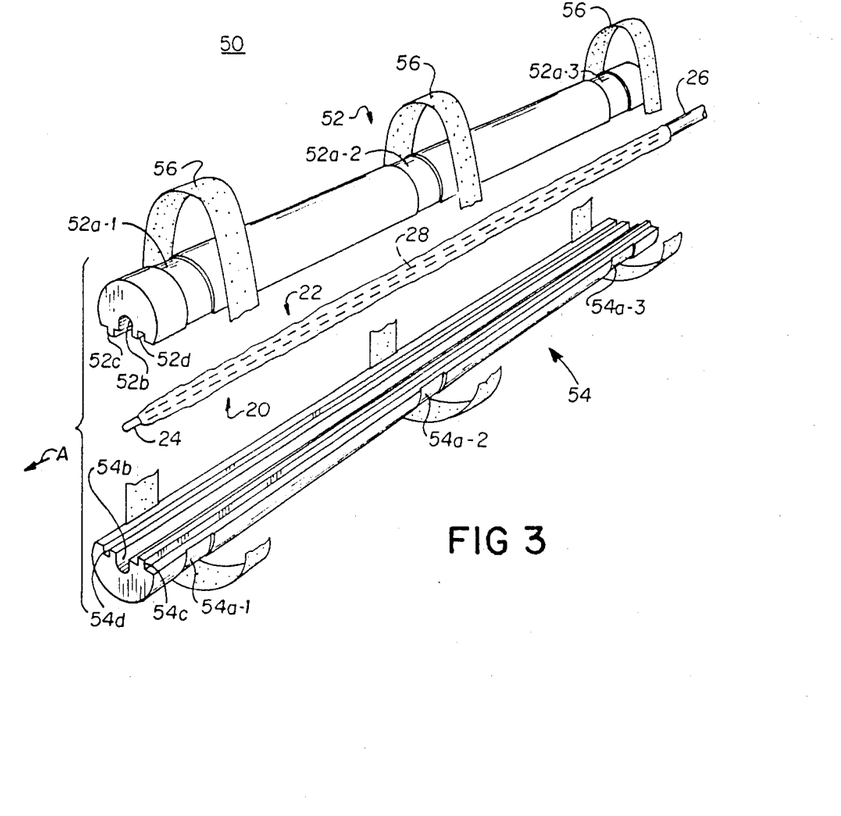
FIG. 3 shows an exploded perspective view of a holder assembly embodying the principles of the present invention.

The holder halves 52 and 54 are further provided with elongated semicircular-shaped grooves 52b and 54b and with an elongated projection 52c, 54c along one side of the elongated semicircular grooves 52b, 54b and with an elongated groove 52d, 54d on the opposite side of said semi-circular grooves 52b and 54b.

Figure 3A:
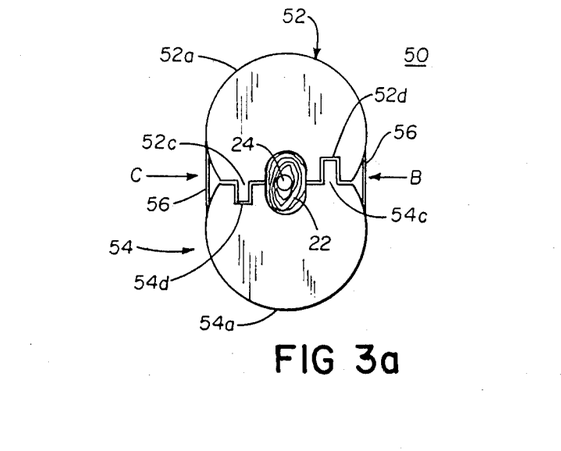
FIG. 3a shows the holder assembly of FIG. 3 in the fully assembled state.

In use, projections 52c and 54c are arranged to fit into grooves 54d and 52d respectively, as shown best in FIG. 3a. When interfitted in this manner, the semicircular-shaped grooves 52b and 54b cooperatively define an elongated hollow annular bore for receiving the wrapped balloon 22.

The holder assembly 50 is used in the following manner:

The balloon 22 is evacuated and wrapped in a tight spiral in the same manner as was previously described. The spirally wrapped balloon 22 is then set into the semi-circular groove 54b, for example, of holder half 54. The other holder half 52 is then interfitted with holder half 54 with the projections of each holder half being inserted into an associated groove of the other holder half, as was described hereinabove.

Holder halves 52 and 54 are retained in the assembled position shown in FIG. 3a by the provision of suitable tie means wrapped about the holder halves after assembly.

In the preferred embodiment shown in FIG. 3, the tie means comprises three plastic strips 56 each forming a closed loop and arranged within the recesses provided about holder halves 52 and 54. For example, it should be noted that recesses 52a-1 and 54a-1 are in alignment when the holder halves 52 and 54 are joined, as shown in FIG. 3a. The left-hand-most strip 56 is seated within these cooperating recesses. The plastic strip 56 is preferably of the heat-shrink type wherein the application of heat causes the closed-loop strip 56 to shrink and thereby tightly encircle holder halves 52 and 54. The remaining strips are arranged within associated cooperating recessed pairs in a similar fashion. It should be understood that any other type of tie means may be provided such as, for example, a strip having a pressure-sensitive adhesive which may be wrapped around each recess one or more times. A soft wire may also be wrapped around each recess, the recesses being designed to accommodate and conform to such a wire.

A holder assembly 50, once fully assembled and retained in the assembled state, serves to retain the balloon 22 tightly wrapped until ready for use.

The holder halves 52, 54 are preferably formed of a plastic material having a very low coefficient of sliding friction. One suitable material is polytetrafluoroethylene. Alternatively, the holder halves may be formed of another material, which may be either plastic or metal and in which at least the elongated semi-circular grooves 52b and 54b are coated with a material providing a low coefficient of sliding friction. Alternatively, or in addition to the low friction surface, the semi-circular groove may be coated with a lubricant which is nontoxic and which has no harmful effect either to the balloon 22 or holder 50, or to the patient.

Figure 4A:
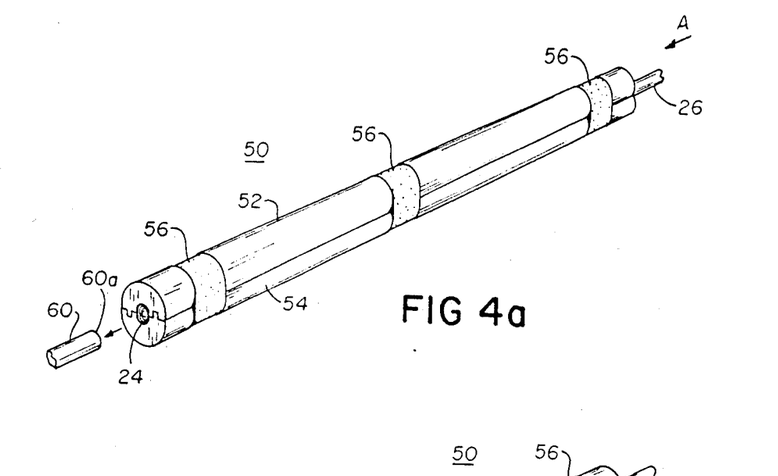
FIGS. 4a and 4b show developmental views of the manner in which the wrapped balloon is withdrawn from the holder assembly of FIG. 3.
Figure 4B:
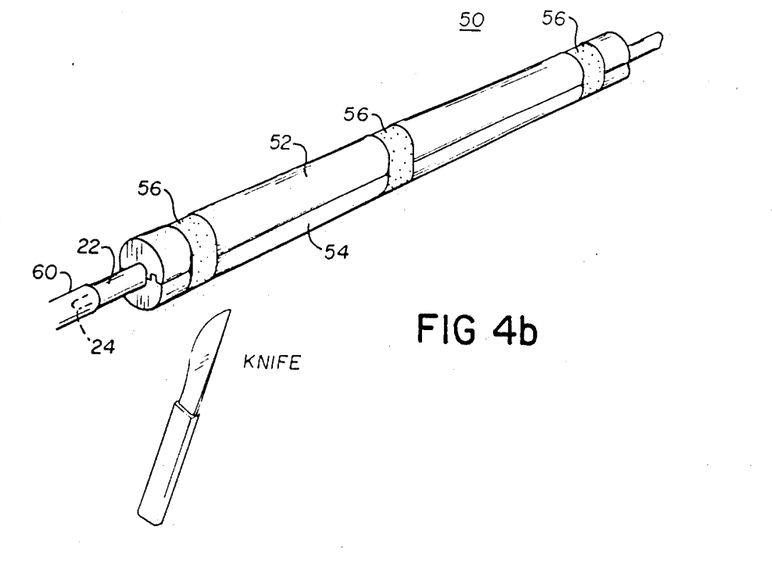

When it is desired to use the balloon assembly 20, for example, for percutaneous insertion into a patient, a sheath 60, shown in FIG. 4a, is inserted into the body of the patient in accordance with the Seldinger technique, for example. Once the sheath is properly inserted in the patient, the balloon 22 is removed from the holder assembly 50 by gripping holder assembly 50 in one hand, gripping catheter tube 26 in the other hand, and moving catheter tube 26 in the direction shown by arrow A relative to holder assembly 50, causing the wrapped balloon 22 to emerge from the left-hand end of holder 50. The tip 24 of the balloon assembly 20 may be placed into the opening 60a in insertion sheath 60 before the balloon 22 is completely removed from holder assembly 50. Catheter tube 26 is moved relative to holder assembly 50 until the balloon is totally moved out of holder assembly 50, whereupon the holder assembly may then be taken apart and discarded. To disassemble the holder assembly, plastic strips 56 may be severed by a sharp knife or other instrument preferably positioned in the region of either joint, as shown by arrows B and C in FIG. 3a. Placing a sharp instrument in this position does not jeopardize the integrity of the balloon assembly 20, since the projections 52c and 54c (FIG. 3a) prevent the knife or other sharp instrument from moving beyond the projection.

The plastic strips 56 are then discarded, and the holder halves 52 and 54 separated from one another and may also be discarded. This arrangement assures that the balloon 22 will be retained tightly wrapped until use, and in addition, provides a simple means for removing the balloon from the holder assembly in readiness for its insertion into a patient.

Still another technique which may be used independently of, or in addition to, holder assembly 50 is comprised of coating the exterior surface of balloon 22 with a sticky substance which causes adjacent exterior surfaces of the balloon 22 to adhere to one another when tightly wrapped. The balloon is retained in the tightly wrapped condition until use and, upon insertion into the patient, the sticky substance is selected to have the characteristic of being quickly and fully dissolved by the blood, and so as to be nontoxic and compatible with the blood to avoid any harm to the patient. One suitable substance is sugar. The sugar may be applied preferably in liquid form by providing a sugar syrup into which the balloon 22 is immersed preparatory to wrapping. The balloon 22 is wrapped in the manner described hereinabove and is retained in the tightly wrapped fashion due to the adhering action of the substance which becomes sticky as it dries. When the substance dries, its bonding characteristics are further strengthened. The balloon is inserted into the insertion sheath 60 in the same manner as was previously described, either directly from a suitable packaging sheath such as a plastic bag, or from holder assembly 50.

As the wrapped balloon 22 enters into the bloodstream, the sticky substance is completely and rapidly dissolved, enabling the balloon to be unwrapped and selectively inflated and deflated. The sugar is nontoxic and has no harmful effect whatsoever upon either the patient or the body fluids.

Since the balloon 22 is mounted in an eccentric manner, i.e. offset from the longitudinal axis of the catheter 26 and balloon tip 24, it may be desirable to know the orientation of the balloon 22 relative to catheter tube 26.

This is accomplished by providing a marking indicia 39 along the periphery of catheter tube 26, as shown in FIG. 2. The indicia 39 represents the angular direction in which balloon 22 extends from the longitudinal axis common to catheter tube 26 and tip 24. Thus, when it is desired to orient balloon 22 within the aortic arch in the angular position which will provide for optimum pumping efficiency, this can be accomplished merely by observing the location of indicia 39 along catheter tube 26, and rotating catheter tube 26 about its central axis, thereby properly orienting balloon 22 in the desired angular position within the aortic arch.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. A balloon assembly adapted for facilitating insertion in a vessel comprising:
   an elongated catheter tube;
   an elongated balloon having a proximal end joined to one end of said catheter tube and having an opposite, distal end terminating in a tip;
   a stylet having a distal end terminating in said tip and extending through said balloon and into said catheter tube;
   said balloon comprising a sleeve having a tapered distal and proximal end respectively joined to said tip and said catheter tube;
   said balloon assuming an annular cross-section when uninflated and being generally symmetric about an imaginary longitudinal axis; and
   said tapered distal and proximal ends joining said balloon to said tip and said catheter tube and aligning said stylet so that said stylet is substantially displaced from the longitudinal axis of said balloon to facilitate tight wrapping of the balloon about said stylet.

2. The balloon assembly of claim 1 wherein the apex of each of said tapered balloon ends are both offset from said balloon longitudinal imaginary axis.

3. The balloon assembly of claim 1 wherein said tapered balloon ends have one tapered portion and one straight portion substantially forming a right angle imaginary cone.

4. The balloon assembly of claim 1 wherein the balloon has an oval cross-section defined by a pair of flat surface portions joined to a pair of curved portions, the ends of said balloon being adjacent one of said curved portions and being joined to said tip and catheter tube so that the stylet engages the interior surface of one of said curved portions.

5. The balloon assembly of claim 1 wherein the tapered ends of the balloon terminate in openings communicating with said tip and said catheter tube to place the stylet extending therethrough in close proximity with the interior surface along substantially the entire length of the balloon.

6. The balloon assembly of claim 4 wherein the remaining one of said curved portions is remote from said stylet.

7. The balloon assembly of claim 1 wherein said stylet is secured to said tip.

8. The balloon assembly of claim 7 further comprising coupling means joined to the proximal end of said catheter tube;
   said stylet extending through said catheter tube and into said coupling means;
   said coupling means including twisting means having a rotatable control knob; and
   the proximal end of said stylet being coupled to said twisting means for rotating said stylet.

9. A method for preparing an intra-aortic balloon assembly for insertion into the body, said balloon assembly comprising a catheter tube and a balloon having a proximal end joined to the distal end of the catheter tube and having a distal end terminating in a tip; a stylet extending through said balloon and having a distal end terminating in said tip and a proximal end extending into the catheter tube; the balloon openings communicating with said tip and said catheter tube to hold the stylet is displaced from the longitudinal axis of the balloon, said method comprising the steps of:
   evacuating the balloon assembly sufficient to collapse the balloon so that the balloon assumes a flat tape-like cross-section, defined by a pair of flat portions joined at their ends along folds, said stylet lying against the interior of one of said folds; and
   wrapping the balloon in a tight spiral about the stylet.

10. The method of claim 9 wherein the wrapping step further comprises the steps of wrapping the balloon several times about the stylet; releasing and reapplying the vacuum condition and thereafter wrapping the balloon several more turns about the stylet; and repeating the last-mentioned step until the balloon is completely wrapped about the stylet.

11. The method of claim 10 further comprising the step of encasing the wrapped balloon in a holder.

12. The method of claim 11 further comprising the step of pushing the balloon out of the holder preparatory to insertion of the balloon into the body.

13. The method of claim 12 further comprising the step of inserting the distal end of the balloon into a sheath as it emerges from said holder.

14. The method of claim 13 further comprising the step of removing the holder from the balloon assembly after the balloon has completely emerged from the holder.

15. The method of claim 9 further comprising the step of introducing a lubricant into the interior of the balloon to facilitate sliding engagement between interior surfaces of the balloon as it is being wrapped to facilitate a tight wrap.

16. The method of claim 15 wherein the lubricant is water.

17. The method of claim 15 wherein the lubricant is a powdered lubricant.

18. The method of claim 9 further comprising the step of dipping the balloon into a solution containing a material which when dry, causes the adjacent external surfaces of the balloon to adhere to one another, said material being dissolved when placed in the bloodstream.

19. An intra-aortic balloon assembly comprising:
   an elongated balloon having an annular cross-section generally concentric about a longitudinal axis; said balloon having distal and proximal ends terminating in openings which are offset from said longitudinal axis;
   a catheter tube;
   the proximal end of said balloon being joined to the distal end of said catheter tube;

the distal end of said balloon terminating in a tip;
a stylet having a distal end positioned in said tip and extending through said balloon distal and proximal ends and into said catheter tube;
said stylet extending generally along the centers of said distal and proximal ends and being offset from the longitudinal axis of said balloon.

20. An intra-aortic balloon assembly comprising a catheter tube;
an elongated balloon having an annular cross-section;
the ends of said balloon terminating in openings;
the intermediate portion of said balloon being substantially uniform in diameter, said openings having diameters substantially smaller than the diameter of said balloon intermediate portion;
said openings being offset from said longitudinal axis;
the proximal end of said balloon being joined to the distal end of said catheter tube;
the distal opening of said balloon terminating in a tip;
a stylet extending through said catheter tube, said proximal opening, said balloon, said distal opening and terminating in said tip; and
said balloon openings positioning said stylet offset from said longitudinal axis.

21. The intra-aortic balloon assembly of claim 20, wherein said stylet is affixed to the interior surface of said balloon.

22. The intra-aortic balloon assembly of claim 20 wherein said stylet is embedded in the wall of said catheter tube.

23. The intra-aortic balloon assembly of claim 20 wherein said catheter tube is comprised of inner and outer concentric tubes; and
said stylet positioned between the engaging surfaces of said tubes.

24. The intra-aortic balloon assembly of claim 20 wherein a lubricant is provided in the interior of said balloon.

25. The intra-aortic balloon assembly of claim 24, wherein said lubricant is water.

26. The intra-aortic balloon assembly of claim 24, wherein said lubricant is a silicone powder.

27. The balloon assembly of claim 20 further comprising coupling means joined to the proximal end of said catheter tube;
said stylet extending through said catheter tube and into said coupling means;
said coupling means including twisting means having a rotatable control knob;
the proximal end of said stylet being coupled to said twisting means for rotating said stylet.

28. An intra-aortic balloon assembly comprising a balloon having a distal end and a proximal end;
a catheter tube having a distal end joined to the proximal end of said balloon;
the distal end of the balloon terminating in a tip;
a stylet extending between said tip and the proximal end of said catheter tube;
the ends of the balloon being offset from the intermediate portion of said balloon to displace the stylet from the longitudinal axis of the balloon so that when the balloon is collapsed to a flat configuration defined by first and second flat portions joined by a pair of spaced elongated folds, said stylet is positioned adjacent the interior of one of said folds to facilitate the formation of one continuous spiral wrapping of the flattened balloon about the stylet.

29. The intra-aortic balloon assembly of claim 28 wherein said stylet is a hollow tubular member.

30. The intra-aortic balloon assembly of claim 29 wherein said tip has an opening communicating with the hollow interior of said tubular stylet to permit insertion of a guide wire therethrough.

31. The intra-aortic balloon assembly of claim 28 further comprising a locating indicia on the exterior of said catheter at a location sufficiently remote from said balloon to indicate the direction which the balloon extends away from said stylet to facilitate proper orientation of the balloon within the body.

32. The intra-aortic balloon assembly of claim 28 further comprising a locating indicia on the exterior of a coupling joined to said catheter at a location sufficiently remote from said balloon to indicate the direction which the balloon extends away from said stylet to facilitate proper orientation of the balloon within the body.

33. The apparatus of claim 32 wherein said sticky substance is nontoxic to the patient.

34. The intra-aortic balloon of claim 28 wherein a sticky substance is deposited upon the exterior surface of said balloon to cause the balloon, when wrapped after application of said substance, to retain said wrapped condition; and
said sticky substance being dissolvable in the bloodstream to release the balloon from the wrapped condition when the wrapped balloon is inserted into the body.

* * * * *